(12) United States Patent
Itoh

(10) Patent No.: US 7,510,683 B2
(45) Date of Patent: Mar. 31, 2009

(54) SAMPLE-CONVEYING SYSTEM HAVING MOBILE UNIT

(75) Inventor: Teruaki Itoh, Kumamoto (JP)

(73) Assignee: IDS Co., Ltd., Kumamoto (JP)

( * ) Notice: Subject to any disclaimer, the term of this patent is extended or adjusted under 35 U.S.C. 154(b) by 750 days.

(21) Appl. No.: 11/100,469

(22) Filed: Apr. 7, 2005

(65) Prior Publication Data

US 2005/0265896 A1    Dec. 1, 2005

(30) Foreign Application Priority Data

Apr. 12, 2004  (JP) ............................ 2004-117125

(51) Int. Cl.
    *G01N 35/04*    (2006.01)
(52) U.S. Cl. .......................................... 422/65; 422/63
(58) Field of Classification Search ................. 422/100, 422/63, 65
    See application file for complete search history.

(56) References Cited

U.S. PATENT DOCUMENTS 4,698,775 A * 10/1987 Koch et al. ................. 700/218
5,350,564 A * 9/1994 Mazza et al. .................. 422/63
6,609,872 B2 * 8/2003 Itoh ............................ 414/390
2003/0044319 A1 * 3/2003 Itoh ............................. 422/63

FOREIGN PATENT DOCUMENTS

| JP | 2001-278409 | * 10/2001 |
| JP | 2001-124786 | * 11/2001 |
| JP | 2002-137822 | 5/2002 |

* cited by examiner

*Primary Examiner*—Jill Warden
*Assistant Examiner*—Monique Mirabeau
(74) *Attorney, Agent, or Firm*—Nixon & Vanderhye P.C.

(57) ABSTRACT

A sample-conveying system has first and second conveying paths which are separated from each other. A first transition base is located at a conveyance terminal end portion of the conveying path. A second transition base is located at a conveyance starting end portion of the conveying path. A mobile unit moves between the first and second conveying paths. The transition base is provided with a receptacle carrier and a rack carrier. The receptacle carrier transfers receptacles on the conveying path to a rack on the transition base. The rack carrier transfers the rack on the transition base onto the mobile unit. The transition base is provided with a rack carrier and a receptacle carrier. The second rack carrier transfers the rack on the mobile unit onto the transition base. The second receptacle carrier transfers each receptacle held in the rack to a holder in the conveying path.

4 Claims, 5 Drawing Sheets

SAMPLE-CONVEYING SYSTEM HAVING MOBILE UNIT

CROSS-REFERENCE TO RELATED APPLICATIONS

This application is based upon and claims the benefit of priority from prior Japanese Patent Application No. 2004-117125, filed Apr. 12, 2004, the entire contents of which are incorporated herein by reference.

BACKGROUND OF THE INVENTION

1. Field of the Invention

This invention relates to a sample-conveying system having a belt-conveyor type conveying mechanism for conveying a holder that holds a receptacle, such as a test tube, which contains blood to be tested.

2. Description of the Related Art

Generally, in a sample-conveying system having a belt conveyor, long conveying paths of complicated forms are arranged substantially throughout the installation space of the system, depending on the purpose of use. Many long conveying paths may block passages for operators and work vehicles. If samples must be moved over a long distance, moreover, long conveying paths sometimes may be arranged for conveyance only, although the samples are not processed in the middle of the conveying paths.

Sample-conveying systems using mobile units have been proposed to solve this problem. One such system is described in Jpn. Pat. Appln. KOKAI Publication No. 2002-137822. The conventional sample-conveying system using a mobile unit includes a belt-conveyor type conveying mechanism having first and second conveying paths that are separated from each other. This conveying mechanism has holders for holding receptacles that contain samples. To convey these holders, the mobile unit moves between a conveyance terminal end portion of the first conveying path and a conveyance starting end portion of the second conveying path. The mobile unit is guided by a guide member as it runs.

The mobile unit that is used in the conventional sample-conveying system described above has a conveying lane on its upper surface. The conveying lane is connected alternatively to respective conveying lanes of the first and second conveying paths. One or several holders that hold the receptacles are delivered at a time from the conveyance terminal end portion of the first conveying path to the conveying lane of the mobile unit. These holders are conveyed to the second conveying path by the mobile unit. Then, they are delivered from the conveying lane of the mobile unit to the conveyance starting end portion of the second conveying path. In order to feed many holders from the first conveying path to the second conveying path by the sample-conveying system, the mobile unit must frequently move between the first and second conveying paths. If the space between the first and second conveying paths is utilized as a passage for an operator or work vehicle, in the conventional sample-conveying system of this type, the mobile unit causes danger as it passes through the passage frequently.

BRIEF SUMMARY OF THE INVENTION

The object of this invention is to provide a sample-conveying system, capable of lowering the frequency of movement of a mobile unit between a first conveying path and a second conveying path and enhancing the safety of utilization of a space between the first and second conveying paths as a passage for an operator or work vehicle.

In a sample-conveying system according to this invention, a belt-conveyor type conveying mechanism for conveying a holder which holds a receptacle with sample is composed of a first conveying path and a second conveying path which are separated from each other. Further, the sample-conveying system according to this invention is constructed in the following manner:

(a) A first transition base having a first loading deck is located at a conveyance terminal end portion of the first conveying path, and a second transition base having a second loading deck is located at a conveyance starting end portion of the second conveying path. A mobile unit is located between the first transition base and the second transition base. The mobile unit is guided by a guide member as it moves.

(b) A first receptacle carrier is provided on the first transition base and serves to transfer a given number of receptacles with samples, which are conveyed to the conveyance terminal end portion of the first conveying path, to an empty rack on the first loading deck at a time. Further, a first rack carrier is provided on the first transition base and serves to transfer the rack on the first loading deck to a loading deck of the mobile unit.

(c) A second rack carrier is provided on the second transition base and serves to transfer the rack conveyed by the mobile unit from the mobile unit to the second loading deck. Further, a second receptacle carrier is provided on the second transition base and serves to transfer a given number of receptacles with samples from the rack on the second loading deck at a time to holders in the second conveying path.

The receptacles with samples, along with the holders, are conveyed along the first conveying path to the first transition base. On the first transition base, a given number of receptacles with samples are taken from the holders at a time by the first receptacle carrier. These receptacles with samples are inserted into the rack on the first loading deck of the first transition base. As this operation is repeated several times, the rack is filled with the receptacles with samples. The rack that holds these receptacles is transferred from the first loading deck to the mobile unit by the first rack carrier. The mobile unit moves from the first transition base to the second transition base and is situated beside the second transition base. The rack on the mobile unit is transferred from the mobile unit to the second loading deck of the second transition base by the second rack carrier. A given number of receptacles with samples are taken from the rack on the second loading deck at a time by the second receptacle carrier. The receptacles with samples taken from the rack are inserted into the holders that are fed to the conveyance starting end portion of the second conveying path.

According to the sample-conveying system of the invention that is constructed and operates in this manner, the frequency of movement of the mobile unit between the first and second conveying paths can be lowered. Thus, the time during which a space between the first and second conveying paths can be utilized as a passage for an operator or work vehicle can be lengthened, so that the safety of utilization of the passage is enhanced.

Each of the first and second receptacle carriers may comprise a hand mechanism having chuck members capable of holding a plurality of receptacles with samples, a cylinder mechanism which raises and lowers the hand mechanism, a guide which extends at right angles to the first or second conveying path, and a chain mechanism which moves the hand mechanism and the cylinder mechanism along the guide.

Each of the first and second rack carriers should preferably comprise a rack hanger having a rack supporting portion capable of being brought under or evacuated from under the rack, a cylinder mechanism which raises and lowers the rack hanger, a guide which extends at right angles to the first or second conveying path, a mechanism which moves the rack hanger and the cylinder mechanism along the guide, and a shift drive mechanism which moves the rack supporting portion parallel to the first or second conveying path to bring under or displace the rack supporting portion from under the rack.

The mobile unit should only be configured so as to be movable only in a straight line when the first and second conveying paths are situated on one straight line as viewed from above. If the first and second conveying paths are cranked as viewed from above, the mobile unit should preferably comprise a drive mechanism which drives wheels and a redirecting mechanism which can redirect at least one of the wheels around a vertical axis so that it can follow the cranked guide member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of this invention will now be described with reference to the accompanying drawings.

Figure 1:
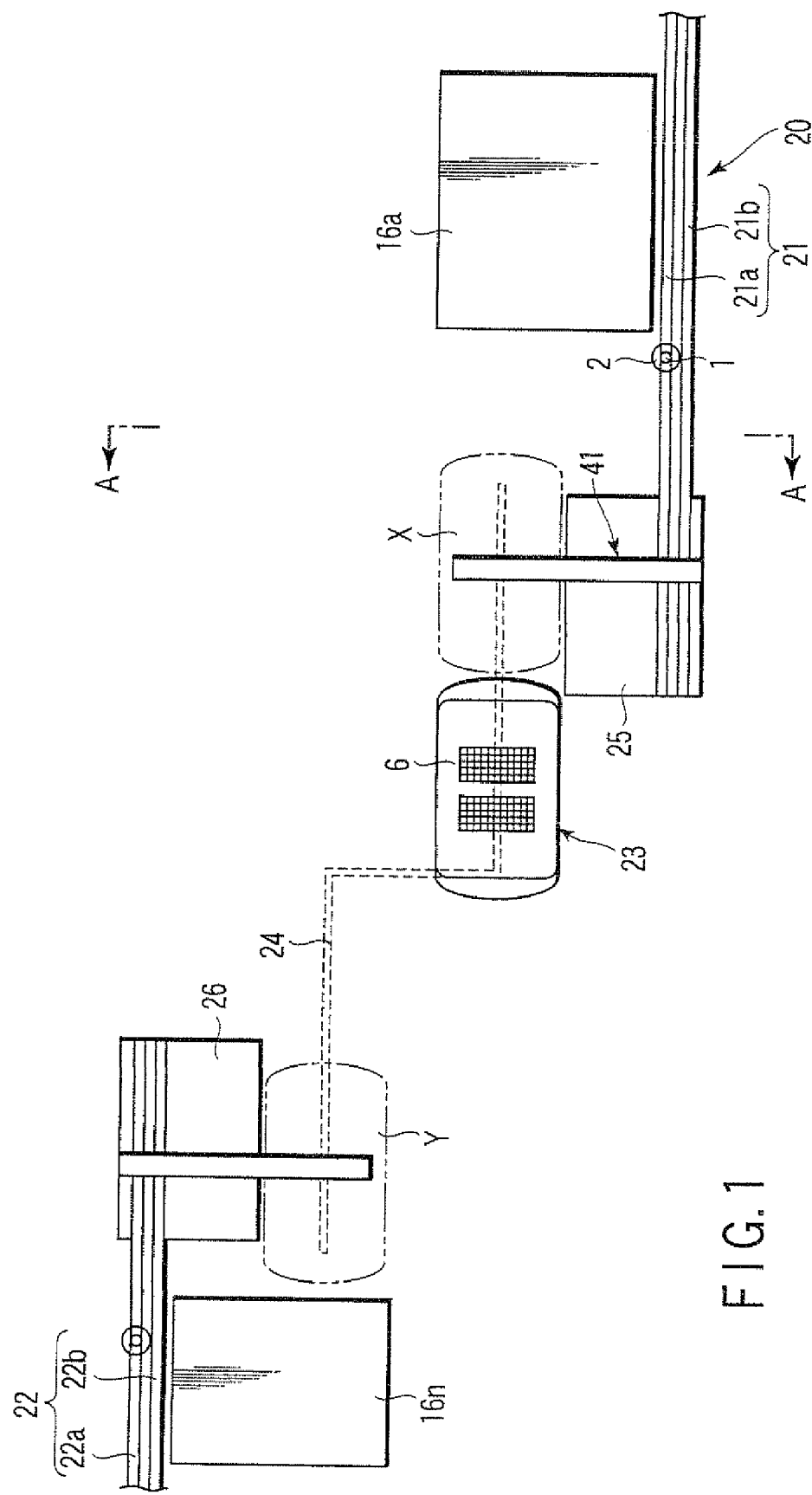
FIG. 1 is a plan view showing an outline of a sample-conveying system according to an embodiment of the invention.

As shown in FIG. 1, a sample-conveying system of the present embodiment comprises a belt-conveyor type conveying mechanism 20 for conveying holders 2. Each holder 2 holds a receptacle 1, such as a test tube, which contains blood to be tested. The conveying mechanism 20 is composed of a first conveying path 21 and a second conveying path 22 that are separate from each other. A mobile unit 23 is located between the first and second conveying paths 21 and 22. The mobile unit 23 is guided by a guide member 24 as it moves.

A first transition base 25 having a first loading deck 25a is provided at a conveyance terminal end portion of the first conveying path 21. A second transition base 26 having a second loading deck 26a is provided at a conveyance starting end portion of the second conveying path 22. The guide member 24 is, for example, a magnetic tape that is attached to a floor. The guide member 24 is located extending between a first transition position X, in which the mobile unit 23 is situated beside the first transition base 25, and a second transition position Y, in which the mobile unit 23 is situated beside the second transition base 26. The movement of the mobile unit 23 is guided by the guide member 24.

As shown in FIG. 1, a sample processing unit 16a is located adjacent to the first conveying path 21. Another sample processing unit 16n is located adjacent to the second conveying path 22. The first conveying path 21 is composed of two conveying lanes 21a and 21b. The second conveying path 22 is also composed of two conveying lanes 22a and 22b.

Figure 2:
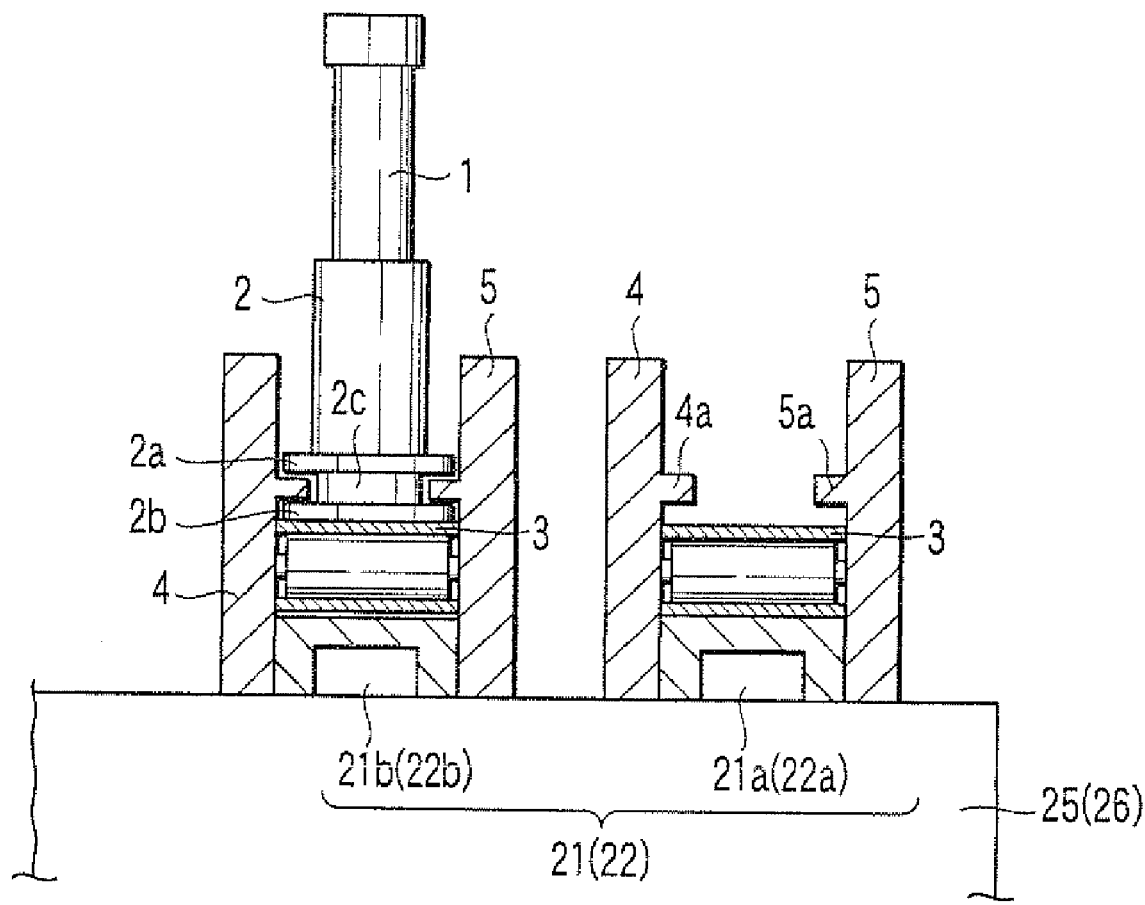
FIG. 2 is a longitudinal sectional view showing first and second conveying paths of the sample-conveying system.

As shown in FIG. 2, each holder 2 has a pair of flanges 2a and 2b and an annular groove 2c defined between them. Each of the conveying lanes 21a, 21b, 22a and 22b has a belt conveyor 3, guide rails 4 and 5, and guide ridges 4a and 5a. The conveyor 3 intermittently moves at regular intervals. The rails 4 and 5 are provided on either side of the conveyor 3. The annular groove 2c of the holder 2 engages the ridges 4a and 5a.

Figure 3:
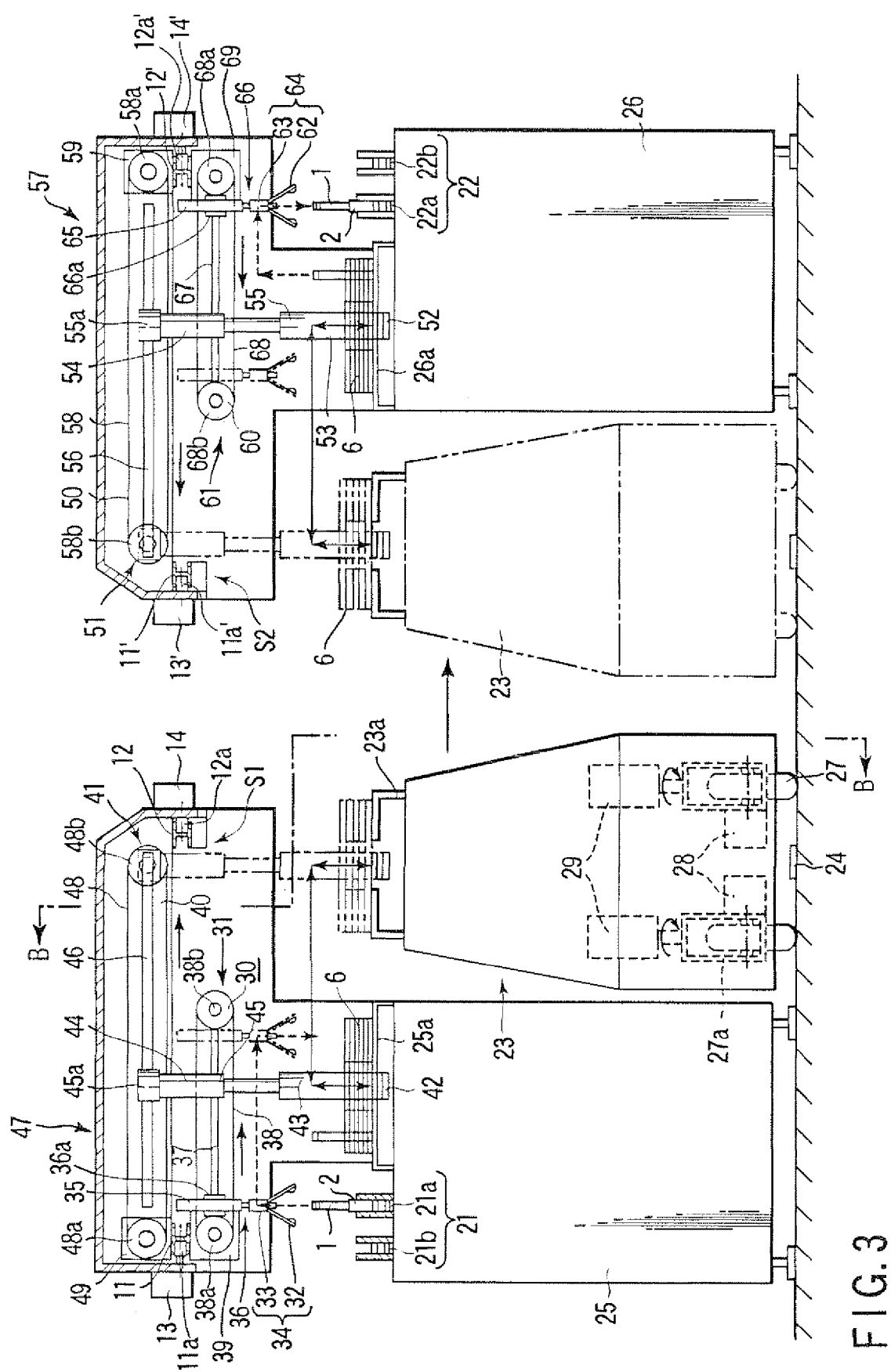
FIG. 3 is a sectional view of the sample-conveying system taken along line A-A of FIG. 1.

As shown in FIG. 3, a loading deck 23a that can carry a plurality (e.g., two) of racks 6 (mentioned later) is formed on the upper surface of the mobile unit 23. The mobile unit 23 should only be configured so that its front and rear wheels can run straight when the first and second conveying paths 21 and 22 are spaced and situated on one straight line as viewed from above.

The guide member 24 shown in FIG. 1 is designed so that the first and second conveying paths 21 and 22 are staggered in the horizontal direction. The guide member 24 is cranked as viewed from above. In this case, the mobile unit 23 is provided with wheels 27 (shown in FIG. 3) that can be redirected around vertical axes so as to be movable along the guide member 24.

The mobile unit 23 has an electric motor 28 as a drive source for rotating the wheels 27, members 27a that support the wheels 27, servomotors 29 for redirecting the wheels 27, a sensor (not shown), etc. The members 27a that support the wheels 27 can be turned around vertical axes. The servomotors 29 serve as redirecting mechanisms for redirecting the wheels 27 around the vertical axes. The sensor detects information that is recorded in the guide member 24. When the electric motor 28 and the servomotors 29 are driven after the guide member 24 is detected by the sensor, the mobile unit 23 moves along the cranked guide member 24. The mobile unit 23 moves between the first transition position X of the first transition base 25 and the second transition position Y of the second transition base 26. In the first transition position X, the mobile unit 23 stops at a position adjacent to the first transition base 25. In the second transition position Y, the mobile unit 23 stops at a position adjacent to the second transition base 26.

Figure 4:
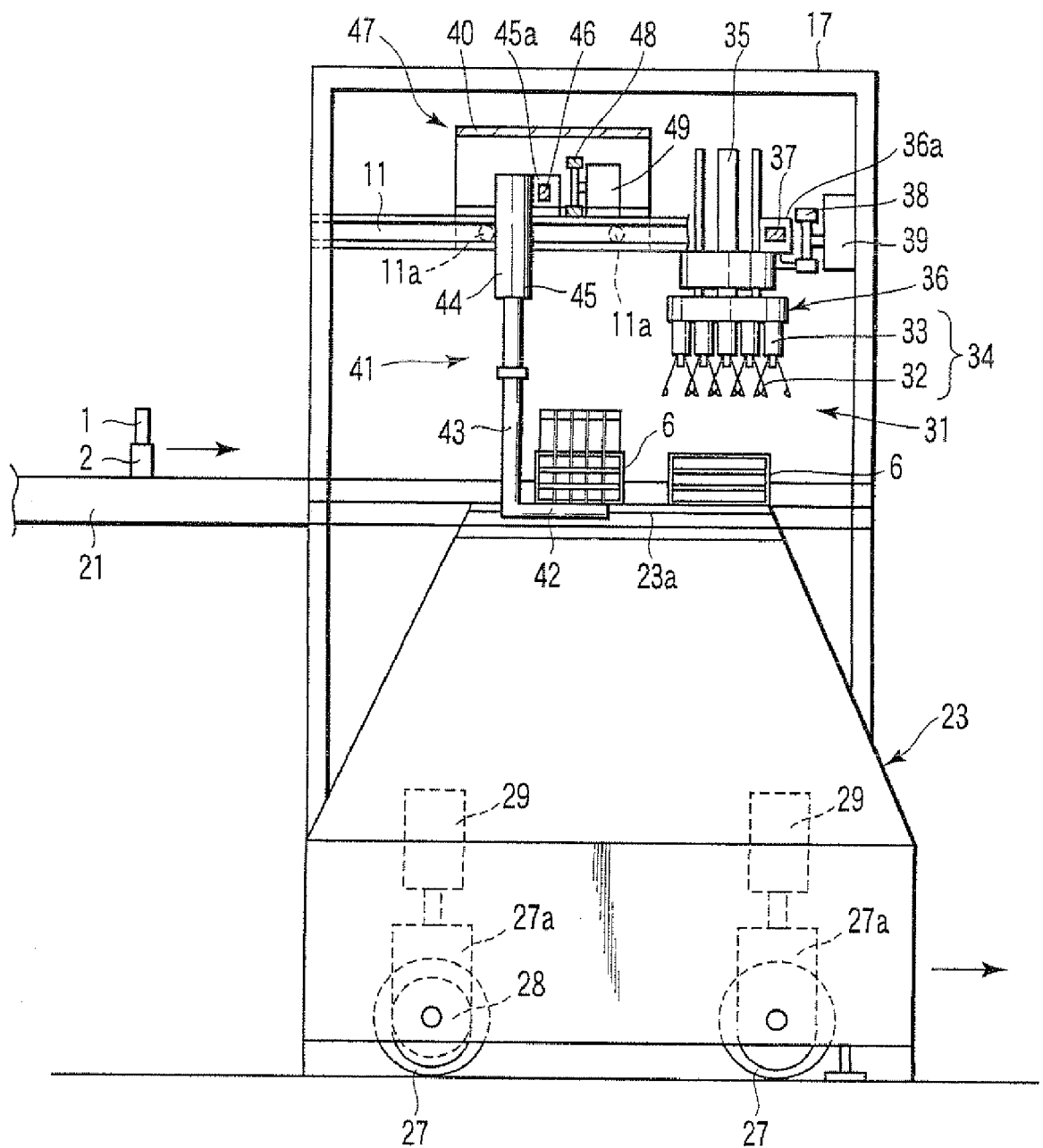
FIG. 4 is a sectional view of the sample-conveying system taken along line B-B of FIG. 3.

As shown in FIGS. 3 and 4, a first receptacle carrier 31 and a first rack carrier 41 are arranged over the first transition base 25. The first receptacle carrier 31 serves to transfer a given number of receptacles 1 with samples, which are conveyed to the conveyance terminal end portion of the first conveying path 21, at a time to an empty rack 6 that is fed onto the first loading deck 25a. The empty rack 6 can hold a large number of receptacles (50 receptacles in the present embodiment). The first rack carrier 41 serves to transfer the rack 6 on the first loading deck 25a onto the loading deck 23a of the mobile unit 23 that stops at the first transition position X.

Figure 5:
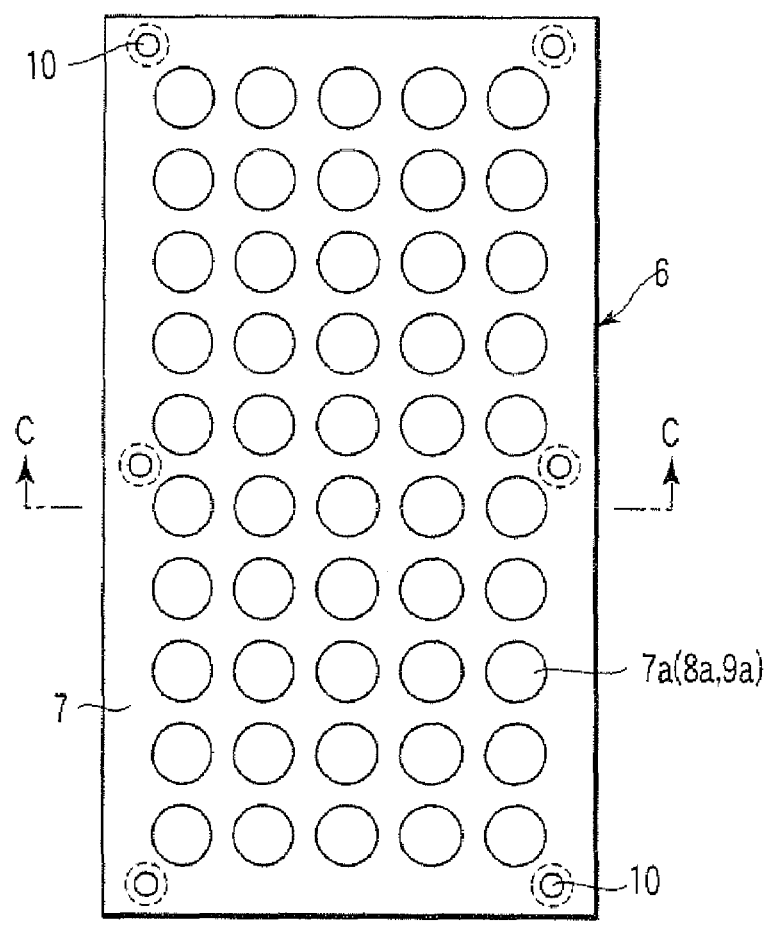
FIG. 5 is a plan view of an empty rack used in the sample-conveying system.
Figure 6:
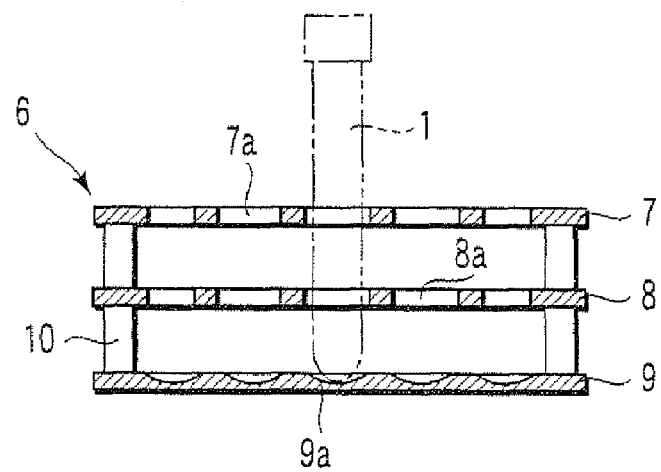
FIG. 6 is a sectional view of the rack taken along line C-C of FIG. 5.

As shown in FIGS. 5 and 6, each rack 6 has upper, middle, and lower plates 7, 8 and 9, which are vertically spaced from one another, and a plurality of connecting rods 10 that connect the plates 7, 8 and 9. Receptacle insertion holes 7a and 8a are formed in the upper and middle plates 7 and 8, respectively. The holes 7a and 8a are formed in 10 longitudinal rows and in 5 transverse rows, for example, and are 50 in total number. Corresponding to these receptacle insertion holes 7a and 8a, individually, 50 recesses 9a are formed in the lower plate 9.

The receptacle carrier 31 comprises a hand mechanism 34 and a cylinder mechanism 35 that vertically moves the hand mechanism 34. The hand mechanism 34 includes five chuck members 32 and cylinder mechanisms 33 that open and close the chuck members 32. The chuck members 32 can simultaneously hold a plurality (e.g., two) of adjacent receptacles 1 with samples. The chuck members 32 and the cylinder mechanisms 33 constitute a hand unit 36.

Further, the receptacle carrier 31 comprises a horizontally extending guide 37, a slider 36a that moves horizontally along the guide 37, and an electric chain mechanism 30 (shown in FIG. 4) that moves the slider 36a. The hand unit 36 is attached to the slider 36a. The guide 37 extends at right angles to the first conveying path 21.

The chain mechanism 30 includes a drive sprocket 38a, a driven sprocket 38b, an endless chain 38 passed around the sprockets 38a and 38b, and a motor 39 for rotating the drive sprocket 38a. The motor 39 can rotate in both forward and reverse directions. The hand unit 36 is connected to the endless chain 38. When the endless chain 38 moves, therefore, the hand unit 36 moves at right angles to the first conveying path 21 along the guide 37.

The first receptacle carrier 31 constructed in this manner operates in the following sequence, thereby transferring, e.g., five at a time, the receptacles 1 with samples delivered from the first conveying path 21 to the first transition base 25 to the empty rack 6 on the first transition base 25. The empty rack 6 is previously fed onto the first loading deck 25a of the first transition base 25. The empty rack 6 can hold, e.g., 50 receptacles with samples.

The receptacles 1 with samples, along with the holders 2, are conveyed to the conveyance terminal end portion of the first conveying path 21, and are stopped adjoining one another at the conveyance terminal end portion by a stopper mechanism (not shown). When the chuck members 32 are closed as the hand mechanism 34 descends, the five receptacles 1 with samples are simultaneously held by the chuck members 32. Thereafter, the hand mechanism 34 ascends. Thereupon, the receptacles 1 are drawn out of their corresponding holders 2. As the hand mechanism 34 descends toward the empty rack 6 after the hand unit 36 is moved horizontally along the guide 37, the five receptacles 1 with samples are simultaneously inserted into the empty rack 6. When the chuck members 32 open, thereafter, the receptacles 1 are released. As this operation is repeated, the 50 receptacles 1 with samples are held in the rack 6.

As the stopper mechanism performs release operation, the empty holder 2 that remains in the conveying lane 21a of the first conveying path 21 is released from the stopper mechanism. The empty holder 2 drops into a holder receiving box (not shown) through an opening (not shown) at the conveyance terminal end portion of the first conveying path 21. The empty holder 2 recovered in this manner is fed to the conveyance starting end portion of the second conveying path 22.

The rack carrier 41 comprises a rack hanger 43 and a cylinder mechanism 44 that vertically moves the hanger 43. The rack hanger 43 and the cylinder mechanism 44 constitute a hanger unit 45. As shown in FIG. 4, the rack hanger 43 has a rack supporting portion 42 that can get under each rack 6.

Further, the rack carrier 41 comprises a horizontally extending guide 46, a slider 45a that moves horizontally along the guide 46, and an electric chain mechanism 40 that moves the slider 45a. The hanger unit 45 is attached to the slider 45a. Thus, the rack supporting portion 42 can move at right angles to the first conveying path 21 along the guide 46.

As shown in FIG. 3, the chain mechanism 40 and the hanger unit 45 constitute a shift unit 47 that can move parallel to the first conveying path 21. The shift unit 47 has wheels 11a and 12a. The wheels 11a and 12a are in contact with beam members 11 and 12, respectively. The wheels 11a and 12a are rotated by motors 13 and 14, respectively. The beam members 11 and 12 are provided on a frame 17 shown in FIG. 4 and extend in the horizontal direction. Thus, the shift unit 47 can move parallel to the first conveying path 21 along the beam members 11 and 12. As the shift unit 47 moves along the beam members 11 and 12, the rack supporting portion 42 can be brought under or displaced from under the rack 6. The beam members 11 and 12, wheels 11a and 12a, motors 13 and 14, etc. constitute a first shift drive mechanism S1 for moving the rack supporting portion 42 parallel to the first conveying path 21.

The chain mechanism 40 includes a drive sprocket 48a, a driven sprocket 48b, an endless chain 48 passed around the sprockets 48a and 48b, and a motor 49 for rotating the drive sprocket 48a. The motor 49 can rotate in both forward and reverse directions. The hanger unit 45 is fixed to the endless chain 48. When the endless chain 48 moves, therefore, the hanger unit 45 moves at right angles to the first conveying path 21, that is, in a direction to convey the rack 6.

By operating in the following sequence, the first rack carrier 41 constructed in this manner can transfer the rack 6 that holds the receptacles 1 with samples on the first loading deck 25a to the loading deck 23a of the mobile unit 23. The mobile unit 23 is previously stopped at the first transition position X of the first transition base 25.

First, the rack hanger 43 descends. As the shift unit 47 moves along the beam members 11 and 12, thereafter, the rack supporting portion 42 comes under the rack 6. The rack hanger 43 is raised by the cylinder mechanism 44. The hanger unit 45 moves horizontally along the guide 46 to a position over the mobile unit 23. The rack hanger 43 is lowered by the cylinder mechanism 44. As the shift unit 47 moves along the beam members 11 and 12, the rack supporting portion 42 is displaced from under the rack 6.

As shown in FIG. 3, a second rack carrier 51 and a second receptacle carrier 61 are arranged over the second transition base 26. The second rack carrier 51 serves to transfer the rack 6 that is conveyed by the mobile unit 23 from the mobile unit 23 to the second loading deck 26a of the second transition base 26. The second receptacle carrier 61 serves to draw out a given number of receptacles 1 with samples in the rack 6 on the second loading deck 26a at a time and insert them into the holder 2 that is fed to the conveyance starting end portion of the second conveying path 22.

The second rack carrier 51 is constructed in the same manner as the first rack carrier 41 described above. The second rack carrier 51 comprises a rack hanger 53 and a cylinder mechanism 54 that vertically moves the hanger 53. The rack hanger 53 and the cylinder mechanism 54 constitute a hanger unit 55. The rack hanger 53 has a rack supporting portion 52 that can get under each rack 6.

Further, the rack carrier 51 comprises a horizontally extending guide 56, a slider 55a that moves horizontally along the guide 56, and an electric chain mechanism 50 that moves the slider 55a. The hanger unit 55 is attached to the slider 55a. Thus, the rack supporting portion 52 can move at right angles to the second conveying path 22 (or in the direction to convey the rack 6) along the guide 56.

As shown in FIG. 3, the chain mechanism 50 and the hanger unit 55 constitute a shift unit 57. The shift unit 57 has wheels 11a' and 12a'. The wheels 11a' and 12a' are in contact with beam members 11' and 12', respectively. The wheels 11a' and 12a' are rotated by motors 13' and 14', respectively. The beam members 11' and 12' extend in the horizontal direction. Thus, the shift unit 57 can move parallel to the second conveying path 22 along the beam members 11' and 12'. As the shift unit 57 moves along the beam members 11' and 12', the rack supporting portion 52 can be brought under or displaced from under the rack 6. The beam members 11' and 12', wheels 11a' and 12a', motors 13' and 14', etc. constitute a second shift drive mechanism S2 for moving the rack supporting portion 52 parallel to the second conveying path 22.

The chain mechanism 50 includes a drive sprocket 58a, a driven sprocket 58b, an endless chain 58 passed around the sprockets 58a and 58b, and a motor 59 for rotating the drive sprocket 58a. The motor 59 can rotate in both forward and reverse directions. The hanger unit 55 is fixed to the endless chain 58. When the endless chain 58 moves, therefore, the hanger unit 55 moves at right angles to the second conveying path 22, that is, in the direction to convey the rack 6.

By operating in the following sequence, the rack carrier 51 constructed in this manner can transfer the rack 6 that holds the receptacles 1 with samples on the mobile unit 23 from the mobile unit 23 to the second loading deck 26a of the second transition base 26. The mobile unit 23 is previously stopped at the second transition position Y of the second transition base 26.

First, the rack hanger 53 descends. As the shift unit 57 moves along the beam members 11' and 12', thereafter, the rack supporting portion 52 comes under the rack 6. The rack hanger 53 is raised by the cylinder mechanism 54. The hanger unit 55 moves horizontally along the guide 56 to the second transition base 26. The rack hanger 53 is lowered by the cylinder mechanism 54. As the shift unit 57 moves along the beam members 11' and 12', the rack supporting portion 52 is displaced from under the rack 6.

The second receptacle carrier 61 is constructed in the same manner as the first receptacle carrier 31. The second receptacle carrier 61 comprises a hand mechanism 64 and a cylinder mechanism 65 that vertically moves the hand mechanism 64. The hand mechanism 64 includes five chuck members 62 and cylinder mechanisms 63 that open and close the chuck members 62. The chuck members 62 can simultaneously hold a plurality (e.g., five) of adjacent receptacles 1 with samples which are held in the rack 6 on the second transition base 26. The chuck members 62 and the cylinder mechanisms 63 constitute a hand unit 66.

Further, the receptacle carrier 61 comprises a horizontally extending guide 67, a slider 66a that moves horizontally along the guide 67, and an electric chain mechanism 60 that moves the slider 66a. The hand unit 66 is attached to the slider 66a. The chain mechanism 60, like the aforementioned chain mechanism 30, includes a drive sprocket 68a, a driven sprocket 68b, an endless chain 68 passed around the sprockets 68a and 68b, and a motor 69 for rotating the drive sprocket 68a. The motor 69 can rotate in both forward and reverse directions. The hand unit 66 is connected to the endless chain 68. When the endless chain 68 moves, therefore, the hand unit 66 moves at right angles to the second conveying path 22 along the guide 67.

By operating in the following sequence, the rack carrier 61 constructed in this manner can take, e.g., five receptacles 1 with samples at a time from the rack 6 on the second loading deck 26a and insert them into the empty holder 2 on the second conveying path 22. This holder 2 is previously fed to the conveyance starting end portion of the second conveying path 22.

As the hand mechanism 64 is lowered by the cylinder mechanism 65 so that the chuck members 62 are closed, the five receptacles 1 with samples are held by the chuck members 62. Thereafter, the hand mechanism 64 is raised by the cylinder mechanism 65. The hand unit 66 moves horizontally along the guide 67. As the hand mechanism 64 descends toward the holder 2, moreover, each receptacle 1 is inserted into its corresponding holder 2. When the chuck members 62 open, thereafter, the receptacles 1 are released. The empty rack 6 from which the receptacles 1 are displaced is removed from the second loading deck 26a and fed to the first loading deck 25a of the first transition base 25.

This invention is not limited directly to the embodiment described above, and its components may be embodied in modified forms without departing from the scope or spirit of the invention. Further, various inventions may be made by suitably combining a plurality of components described in connection with the foregoing embodiment. For example, some of the components according to the foregoing embodiment may be omitted. Alternatively, other components may be combined with those of the foregoing embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A sample-conveying system having a belt-conveyor type conveying mechanism for conveying a holder which holds a plurality of receptacles with respective samples therein, the conveying mechanism having a first conveying path and a second conveying path which are separated from each other, the sample-conveying system comprising:

a first transition base having a first loading deck located at a conveyance terminal end portion of the first conveying path;

a second transition base having a second loading deck located at a conveyance starting end portion of the second conveying path;

a mobile unit which has a mobile loading deck and is guided by a guide member in movement between the first transition base and the second transition base;

a first receptacle carrier which is provided on the first transition base and transfers a given number of receptacles with samples, which are conveyed to the conveyance terminal end portion of the first conveying path, to a rack on the first loading deck;

a first rack carrier which is provided on the first transition base and transfers the rack on the first loading deck to the mobile loading deck of the mobile unit;

a second rack carrier which is provided on the second transition base and transfers the rack conveyed by the mobile unit from the mobile unit to the second loading deck; and a second receptacle carrier which is provided on the second transition base and transfers a given number of receptacles with samples from the rack on the second loading deck to the holder fed to the conveyance starting end portion of the second conveying path, wherein the first receptacle carrier comprises a first hand mechanism having first chuck members capable of holding a plurality of receptacles with samples, a first cylinder mechanism which raises and lowers the first hand mechanism, a first guide which extends at right angles to the first conveying path, and a first mechanism which moves the first hand mechanism and the first cylinder mechanism along the first guide, and wherein the second receptacle carrier comprises a second hand mechanism having second chuck members capable of holding a plurality of receptacles with samples, a second cylinder mechanism which raises and lowers the second hand mechanism, a second guide which extends at right angles to the second conveying path, and a second mechanism which moves the second hand mechanism and the second cylinder mechanism along the second guide.

2. The sample conveying system according to claim 1, wherein the first rack carrier comprises a first rack hanger having a first rack supporting portion capable of being brought under or displaced from under the rack, a first cylinder mechanism which raises and lowers the rack hanger, a first guide which extends at right angles to the first conveying path, a first mechanism which moves the first rack hanger and the first cylinder mechanism along the first guide, and a first shift drive mechanism which moves the first rack supporting portion parallel to the first conveying path to bring under or displace the first rack supporting portion from under the rack.

3. The sample conveying system according to claim 1, wherein the second rack carrier comprises a second rack hanger having a second rack supporting portion capable of being brought under or displaced from under the rack, a second cylinder mechanism which raises and lowers the second rack hanger, a second guide which extends at right angles to the second conveying path, a second mechanism which moves the second rack hanger and the second cylinder mechanism along the second guide, and a second shift drive mechanism which moves the second rack supporting portion parallel to the second conveying path to bring under or displace the second rack supporting portion from under the rack.

4. The sample conveying system according to claim 1, wherein the mobile unit comprises a plurality of wheels, a mobile drive mechanism having a motor for driving the wheels, and redirecting mechanisms which redirect the wheels around vertical axes.

\* \* \* \* \*